United States Patent
Chen et al.

(10) Patent No.: US 12,275,709 B2
(45) Date of Patent: Apr. 15, 2025

(54) PROCESS FOR THE PREPARATION OF EXO-TERT-BUTYL N-(3-AZABICYCLO[3.2.1]OCTAN-8-YL) CARBAMATE

(71) Applicant: Hoffmann-La Roche Inc., Little Falls, NJ (US)

(72) Inventors: Weichun Chen, Shanghai (CN); Guocai Zhang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 965 days.

(21) Appl. No.: 17/418,480

(22) PCT Filed: Dec. 24, 2019

(86) PCT No.: PCT/EP2019/087000
§ 371 (c)(1),
(2) Date: Jun. 25, 2021

(87) PCT Pub. No.: WO2020/136188
PCT Pub. Date: Jul. 2, 2020

(65) Prior Publication Data
US 2022/0073469 A1 Mar. 10, 2022

(30) Foreign Application Priority Data

Dec. 27, 2018 (WO) ............... PCT/CN2018/124296
Jun. 27, 2019 (WO) ............... PCT/CN2019/093185

(51) Int. Cl.
C07D 221/22 (2006.01)
(52) U.S. Cl.
CPC ................. *C07D 221/22* (2013.01)
(58) Field of Classification Search
None
See application file for complete search history.

(56) References Cited

U.S. PATENT DOCUMENTS

| | | | |
|---|---|---|---|
| 7,928,232 B2 | 4/2011 | Tani et al. | |
| 10,562,903 B2 | 2/2020 | Bartels et al. | |
| 10,604,517 B2 | 3/2020 | Baumann et al. | |
| 10,730,881 B2 | 8/2020 | Bartels et al. | |
| 10,899,766 B2 | 1/2021 | Bartels et al. | |
| 10,941,147 B2 | 3/2021 | Bartels et al. | |
| 11,319,314 B2 | 5/2022 | Bartels et al. | |
| 11,370,802 B2 | 6/2022 | Ratni et al. | |
| 12,084,461 B2 | 9/2024 | Ratni et al. | |
| 2006/0014957 A1 | 1/2006 | Whritenour et al. | |
| 2022/0056036 A1 | 2/2022 | Frei et al. | |

FOREIGN PATENT DOCUMENTS

| | | |
|---|---|---|
| EP | 3023416 A1 | 5/2016 |
| WO | 1995/31455 | 11/1995 |
| WO | 2005/021536 | * 3/2005 |
| WO | 2005/021536 A2 | 3/2005 |
| WO | 2011/076212 A2 | 6/2011 |
| WO | 2018/118838 A1 | 6/2018 |

OTHER PUBLICATIONS

International Preliminary Report on Patentability—PCT/EP2019/087000 (Report Issuance Date: Jun. 16, 2021; Chapter I),:pp. 1-7 (Jul. 8, 2021).
International Search Report—PCT/EP2019/087000 (w/Written Opinion),:pp. 1-11 (Apr. 20, 2020).
Melancon, B. et al., "Continued optimization of the MLPCN probe ML071 into highly potent agonists of the hM1 muscarinic acetylcholine receptor, available online Mar. 29, 2012" Bioorg Med Chem Lett 22(10):3467-3472 (Mar. 29, 2012).

* cited by examiner

*Primary Examiner* — D Margaret M Seaman
(74) *Attorney, Agent, or Firm* — Vasily Ignatenko

(57) ABSTRACT

The present invention relates to a process for the preparation of a compound (I) or pharmaceutically acceptable salt thereof, which is useful as the key intermediate for the synthesis of compounds for prophylaxis and treatment of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

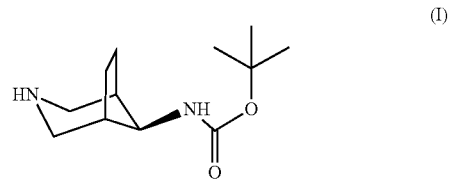

(I)

14 Claims, No Drawings

PROCESS FOR THE PREPARATION OF EXO-TERT-BUTYL N-(3-AZABICYCLO[3.2.1]OCTAN-8-YL) CARBAMATE

The present invention relates to a process for the preparation of a compound (I),

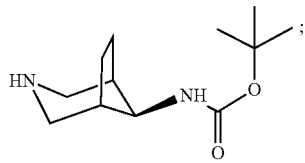

(I)

or pharmaceutically acceptable salt thereof, which is useful as the key intermediate for the synthesis of compounds for prophylaxis and treatment of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

BACKGROUND OF THE INVENTION

The synthetic approach of compound (I) was disclosed in patent WO2018118838 and WO2005021536, however the current processes are not suitable for large scale production due to the following issues:

(a) column purification with tedious work up process is needed for three of the intermediates, such as: 3-benzyl-3-azabicyclo[3.2.1]octan-8-one oxime; 3-benzyl-3-azabicyclo[3.2.1]octan-8-amine; tert-butyl N-(3-benzyl-3-azabicyclo[3.2.1]octan-8-yl)carbamate;

(b) HPLC or SFC chiral separation is necessary, which leads to a large amount of cost;

(c) no report available on removing the excessive $Boc_2O$ in step d) which leads to the major by-product in step e).

Based on the issues above, one object of this invention therefore is to find an efficient synthetic approach which can address all of above issues and be applied on a technical scale.

Another aspect of the present invention relates to a novel process for the preparation of a compound (V) and/or compound (Va):

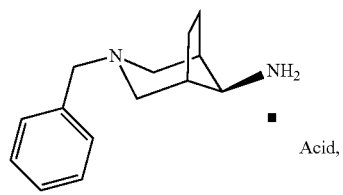

(V)

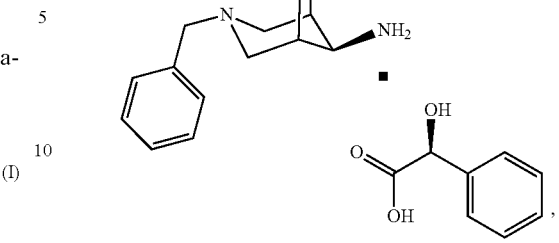

(Va)

wherein the acid is selected from D-glutamic acid, (R)-(−)-Mandelic acid, 1-hydroxy-2-naphthoic acid, citric acid, 4-aminosalicylic acid, L-tartaric acid, hippuric acid, malonic acid, glutaric acid, oxalic acid, fumaric acid, succinic acid, 4-aminobenzoic acid, 2,5-dihydroxybenzoic acid, L-malic acid, salicylic acid, maleic acid, (1S,3R)-(−)-camphoric acid, pamoic acid, mucic acid, palmitic acid, oleic acid and lactobionic acid; particularly the acid is (R)-(−)-Mandelic acid.

DETAILED DESCRIPTION OF THE INVENTION

Definitions

The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457.

Abbreviation

API Active Pharmaceutical Ingredient
DBU 1,8-Diazabicyclo[5.4.0]undec-7-ene
DCM Dichloromethane
DIPEA N,N-Diisopropylethylamine
DMF Dimethylformamide
eq Equivalent
EtOAc or EA Ethyl acetate
IPA Isopropanol IPAc Isopropyl acetate
2-MeTHF 2-Methyltetrahydrofuran
MTBE Methyl tert-butyl ether
NMM N-methylmorpholine
NMP N-Methyl-2-pyrrolidone
Pd/C Palladium on carbon
Pd(OH)/C Palladium hydroxide on carbon
Raney-Ni Raney nickel
TEA Triethylamine
TFA Trifluoroacetic acid
v/v Volume ratio
wt. % Weight percentage The present invention provides a process for preparing the compounds of formula (I) as outlined in the scheme 1.

Step b) the Formation of Compound (VI),

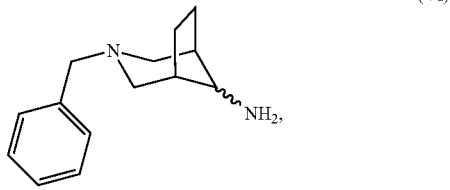

via reduction reaction from compound (III);

Scheme 1

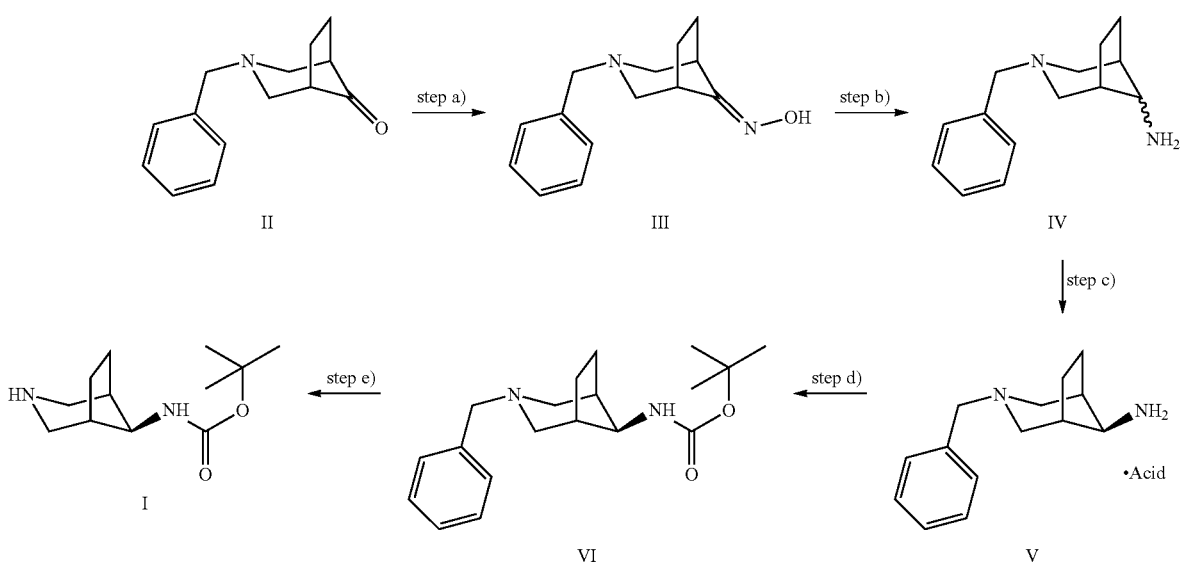

The synthesis comprises the following steps:
Step a) the Imine Formation of Compound (III),

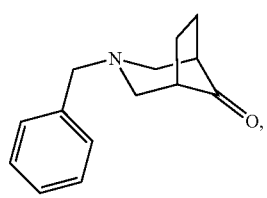

via the reaction of compound (II),

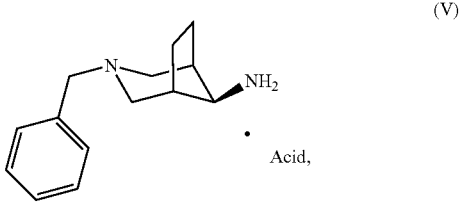

and hydroxylamine hydrochloride;

Step c) the Salt Formation of Compound (V), (V)

from compound (VI) and an acid; wherein the acid is selected from D-glutamic acid, (R)-(−)-Mandelic acid, 1-hydroxy-2-naphthoic acid, citric acid, 4-aminosalicylic acid, L-tartaric acid, hippuric acid, malonic acid, glutaric acid, oxalic acid, fumaric acid, succinic acid, 4-aminobenzoic acid, 2,5-dihydroxybenzoic acid, L-malic acid, salicylic acid, maleic acid, (1S,3R)-(−)-camphoric acid, pamoic acid, mucic acid, palmitic acid, oleic acid and lactobionic acid; particularly the acid is (R)-(−)-Mandelic acid;

Step d) the Formation of Compound (VI),

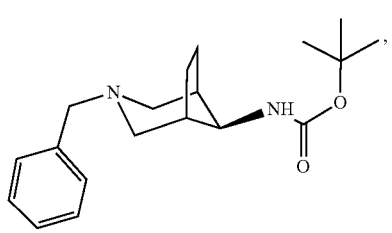
(VI)

via the dissociation and boc-protection reaction of compound (V);

Step e) the Formation of Compound (I),

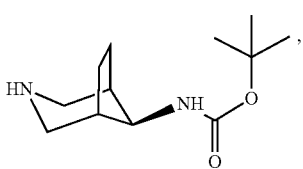
(I)

via the de-protection reaction of compound (VI).

A detailed description of present invention of process steps is as following:

Step a) the Imine Formation of Compound (III),

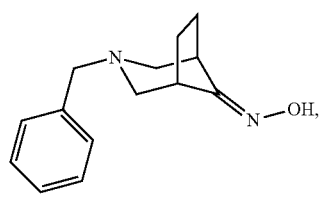
(III)

via the reaction of compound (II),

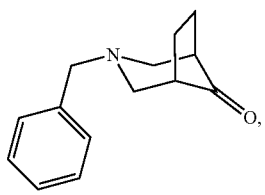
(II)

and hydroxylamine hydrochloride.

Compound of formula (III) is synthesized in the presence of a suitable solvent with a suitable base.

The suitable solvent is selected from MeOH and EtOH; particularly the solvent is EtOH.

The suitable base is selected from KOAc and NaOAc; particularly the suitable base is NaOAc.

The solvent exchange to EtOH after extraction is critical for the whole process in terms of technical scale manufacture. Concentration to remove EA directly gave acceptable yield but this process is unsuitable for large scale manufacture due to safety concern. In present invention, solvent was exchanged to EtOH, which can be controlled for large scale manufacture.

Step b) the Formation of Compound (IV),

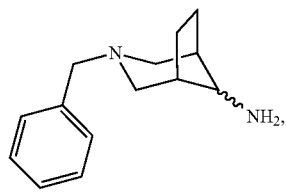
(IV)

via reduction reaction from compound (III).

Compound (IV) is synthesized in a suitable solvent with a suitable reducing reagent.

The suitable solvent is selected from MeOH, EtOH and IPA; particularly the solvent is EtOH.

The suitable reducing reagent is selected from Na, Pd/c and Raney-Ni; particularly the reducing reagent is Raney-Ni.

The reaction is performed at 0° C.-70° C., particularly at 20° C.-30° C.

Temperature is critical for the whole process in terms of endo/exo selectivity. In present invention, step a) and b) are telescoped without solid isolation. The higher temperature (>50° C.) and the lower temperature (<5° C.) during the reduction reaction resulted in low ratio of desired exo product. The temperature system designed in step b) of present invention gives highest yield and good purge effect for impurities.

A series of studies were carried out to demonstrate the impact of reaction temperature, which showed that 20-30° C. is the best condition for the reduction reaction:

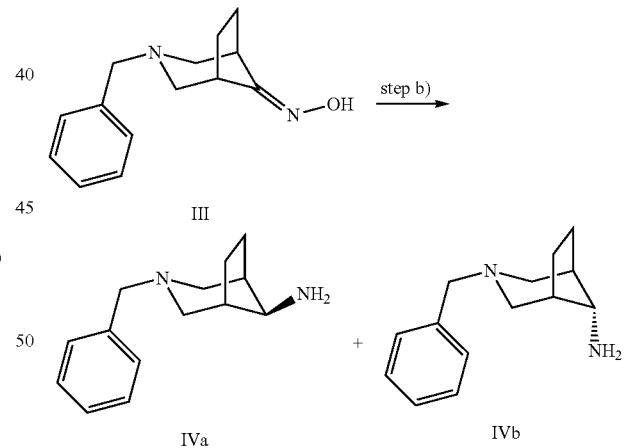

| Test No. | Reaction Condition | IVa: IVb |
|---|---|---|
| 1 | Compound (III) (5.2 g, 1.0 eq.), Raney-Ni (5.2 g, w/w = 1:1), $H_2$ (0.5-0.6 Mpa), EtOH, 16 hr, 0° C. | 0.425 |
| 2 | Compound (III) (5.2 g, 1.0 eq.), Raney-Ni (5.2 g, w/w = 1:1), $H_2$ (0.5-0.6 Mpa), EtOH, 16 hr, 20-30° C. | 0.898 |
| 3 | Compound (III) (5.2 g, 1.0 eq.), Raney-Ni (5.2 g, w/w = 1:1), $H_2$ (0.5-0.6 Mpa), EtOH, 16 hr, 60-70° C. | 0.529 |

Step c) the Salt Formation of Compound (V),

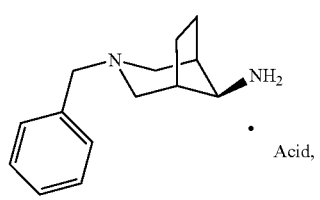

· Acid, from compound (VI) and an acid; wherein the acid is selected from D-glutamic acid, (R)-(−)-Mandelic acid, 1-hydroxy-2-naphthoic acid, citric acid, 4-aminosalicylic acid, L-tartaric acid, hippuric acid, malonic acid, glutaric acid, oxalic acid, fumaric acid, succinic acid, 4-aminobenzoic acid, 2,5-dihydroxybenzoic acid, L-malic acid, salicylic acid, maleic acid, (1S,3R)-(−)-camphoric acid, pamoic acid, mucic acid, palmitic acid, oleic acid and lactobionic acid; particularly the acid is (R)-(−)-Mandelic acid.

Compound of formula (V) is synthesized in the presence of the acid with suitable amount in a suitable organic solvent.

The amount of (R)-(−)-Mandelic acid used in this step is 0.1-2.0 eq., particularly 0.6 eq.

The suitable solvent is selected from MeOH, EtOH, n-propanol, IPA, MeCN, acetone, THF and toluene; particularly the solvent is EtOH.

Step d) the Formation of Compound (VI),

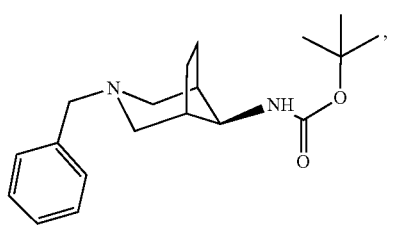

via the dissociation and boc-protection reaction of compound (V).

Compound (VI) in this step is synthesized via dissociation reaction in the presence of a suitable base in a suitable solvent, followed by protected with Boc group. The compound (VI) is purified through recrystallization which was performed in a suitable solvent.

The suitable base used in dissociation reaction is selected from $Na_2CO_3$, $K_2CO_3$, $NaHCO_3$, $KHCO_3$, NaOH and KOH; particularly the base is $K_2CO_3$.

The suitable solvent used in dissociation reaction is selected from IPAc, EtOAc, MTBE, toluene, THF and 2-MeTHF; particularly the solvent is THF.

The recrystallization is performed in a suitable solvent at 20° C.-70° C., particularly at 20° C.-30° C., for 2-48 hrs, particularly for 16 hrs; wherein the suitable solvent is selected from n-heptane, hexane and petroleum ether; particularly the solvent is n-heptane.

Recrystallization in n-heptane is critical for the whole process to improve yield, remove excessive $Boc_2O$ and avoid a di-boc by-product after de-protection removing benzyl group in step e). In present invention, dissociation and protection with Boc group are telescoped without isolation. The recrystallization system designed in this step of present invention gives high yield, good purge effect for impurities and preventing the major by-product

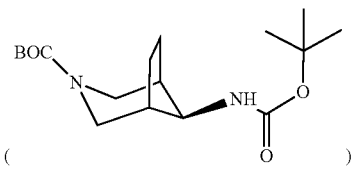

forming in step e) after de-protection reaction due to excessive $Boc_2O$ left from step d).

Step e) the Formation of Compound (I),

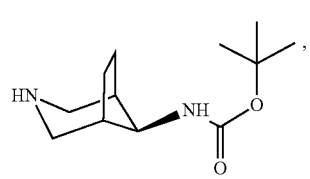

via the de-protection reaction of compound (VI).

Compound of formula (I) is de-protected and synthesized in the presence of a suitable solvent with a suitable reducing reagent.

The suitable solvent is selected from MeOH and EtOH; particularly the solvent is EtOH.

The reducing reagent is selected from hydrogenation with Pd/C and Pd(OH)/C; particularly the reducing reagent is Pd(OH)/C.

The reaction temperature is performed at 20° C.-100° C., particularly at 65° C.-75° C.

EXAMPLES

The invention will be more fully understood by reference to the following examples. They should not, however, be construed as limiting the scope of the invention.

Example 1

3-benzyl-3-azabicyclo[3.2.1]octan-8-one Oxime (Compound III)

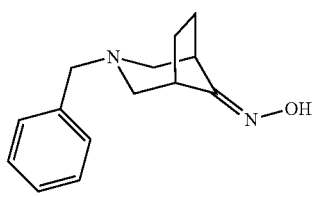 [SMILES: ON=C1C2CCC1CN(Cc1ccccc1)C2]

To a 500 L glass-lined reactor under $N_2$ protection was charged with EtOH (150.00 kg) and 3-benzyl-3-azabicyclo [3.2.1]octan-8-one (compound (II) from Xinlong pharmaceutical, 27 kg, 125.41 mol., 1.00 eq.) at 15° C.~25° C. After being stirred for 30 min, the reaction mixture was charged with hydroxylamine hydrochloride (15.7 kg, 225.93 mol, 1.80 eq.), and sodium acetate (15.4 kg, 187.74 mol, 1.5 eq) in portions slowly to the mixture at 15° C.~20° C. The resulting reaction mixture was heated to 40° C.~50° C. and stirred for another 20 hours, then concentrated to remove part of the solvent to around 60 L~80 L. The residue solution was cooled to 0° C.~5° C. followed by addition of ice water (108 kg) over 20 min at same the temperature range. Then NaHCO$_3$ (32.4 kg) was added to the mixture portion wise over 2 hours at 0° C.~20° C. The resulting reaction mixture was stirred for another hour at 20° C.~25° C. and then extracted with EA (80 kg) 3 times. The combined organic layer was washed with water (54 kg) and 20% wt NaCl aqueous solution (40.5 kg), then filtered through a pad of Na$_2$SO$_4$ (20 kg) and concentrated to remove part of the solvent to 40 L~50 L. The mixture was charged with EtOH (108 kg), then concentrated to 40 L~50 L. EtOH (108 kg) was added again to the residue and concentrated to 50 L~60 L to give a crude product, which was used directly in the next step.

Example 2

3-Benzyl-3-azabicyclo[3.2.1]octan-8-amine (Compound (IV))

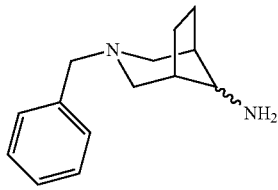 [SMILES: NC1C2CCC1CN(Cc1ccccc1)C2]

To a 1000 L glass-lined reactor was charged with EtOH (270 kg) and 3-benzyl-3-azabicyclo[3.2.1]octan-8-one oxime (compound (III), from Example 1). The formed suspension was degassed under vacuum and purged with N$_2$ for three times followed by addition of Raney-Ni (32 kg, 0.8 wt %) at 15° C.~25° C. The resulting suspension was degassed under vacuum and purged with H$_2$ to 0.5 MPa three times. The reaction mixture was heated to 25° C.~30° C. with stirring for another 14 hours under 0.2 MPa~0.3 MPa H$_2$, then filtered through a MCC (Microcrystalline Cellulose) pad followed by rinsing with EtOH (160 kg) to remove the catalyst. The mother liquor was concentrated to about 180 L left to obtain the crude compounds (IV) which was used for next step reaction without further purification.

Example 3 exo-3-Benzyl-3-azabicyclo[3.2.1]octan-8-amine; (R)-(−)-Mandelic Acid (Compound (Va))

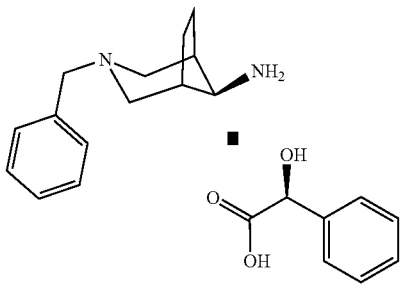

To a 300 L glass-lined reactor with solution of 3-benzyl-3-azabicyclo[3.2.1]octan-8-amine from compound (IV) (180 L) was charged with (R)-(−)-Mandelic acid (12 kg, 78.87 mol, 0.60 eq.) at 60° C.~70° C. After addition, the reaction mixture was stirred at this temperature for another 3 hours, then cooled to 20° C.~25° C. over 4 hours and stirrer for another 7 hours at the same temperature. The solid was separated via centrifuge and the wet cake was washed with EtOH (10 kg) to afford crude product, compound (Va) as a wet cake.

To a 300 L glass-lined reactor was charged with the wet cake and EtOH (126 kg) at 15° C.-25° C. and heated to 80° C.~85° C. with stirring for 6 hours. The solution was cooled to 20° C.~30° C. over 4 hours with stirring for another 16 hours at this temperature. The solid was separated via centrifuge and was washed with EtOH (10 kg), and dried in vacuum oven (30 mmHg, 40° C.) for 32 hours to afford compound (Va) (16 kg, 34.6% yield (3 steps from compound II), 99.65% chiral purity).

Compound (Va): $^1$H NMR (400 MHz, DMSO-d6) δ=7.37-7.12 (m, 11H), 4.51 (s, 1H), 2.99 (s, 1H), 2.60 (dd, J=4.0, 10.7 Hz, 2H), 2.16-2.03 (m, 4H), 1.78-1.70 (m, 2H), 1.70-1.60 (m, 2H)

Example 4 exo-tert-Butyl N-(3-benzyl-3-azabicyclo[3.2.1]octan-8-yl)carbamate (Compound (VI))

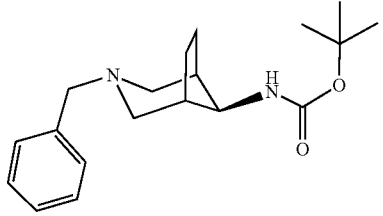

To a 100 L glass-lined reactor was charged with 3-benzyl-3-azabicyclo[3.2.1]octan-8-amine-(R)-(−)-mandelic acid salt (compound (V)), 7 kg, 19.0 mol, 1.00 eq.) portion wise to water (32 kg) solution of K$_2$CO$_3$ (9.17 kg, 66.35 mol, 3.49 eq.) at 20° C.~30° C. The resulting reaction mixture was stirred at 20° C.~30° C. for 0.5 hour and diluted with THF (35 kg) followed by addition of Boc$_2$O (4.97 kg, 22.77 mol, 1.2 eq) dropwise at 20° C.~30° C. over 1.5 hours. After being stirred for another 16 hours at 20° C.~30° C., the reaction mixture was extracted with EtOAc (25 L) three times. The combined organic layer was washed with water (10 kg) three times, dried over Na$_2$SO$_4$ (3.00 kg) for 0.5 hours and then concentrated to remove almost all EtOAc and gave 16 kg crude solid. The crude residue was suspended in n-heptane (10.00 L) and heated to 50° C.~60° C. with stirring for 3 hours. After being cooled to 5° C.~10° C., the mixture was stirred for another 5 hours and filtered. The collected solid was rinsed with n-heptane (5 L) twice and dried under vacuum for 20 hours at 45° C.~50° C. to afford tert-butyl N-(3-benzyl-3-azabicyclo[3.2.1]octan-8-yl)carbamate (compound (VI), 5.60 kg, 1.26 mol, 93.5% yield, 99.68% purity) as an off white solid.

Compound (VI): $^1$H NMR: (400 MHz, CDCl$_3$) δ ppm: 7.22-7.32 (m, 5H), 4.43 (s, 1H), 3.49-3.54 (d, 1H), 2.66-2.71

(dd, 2H), 2.19-2.23 (d, 2H), 2.12 (s, 2H), 1.77-1.84 (dd, 2H), 1.64-1.72 (dd, 2H), 1.46 (s, 9H).

Example 5 exo-tert-Butyl N-(3-azabicyclo[3.2.1]octan-8-yl) carbamate (Compound (I))

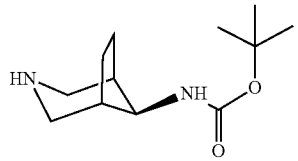

To a 100 L autoclave reactor was charged with EtOH (35.00 L), Pd(OH)/C (350.00 g, 10% wt) and tert-butyl N-(3-benzyl-3-azabicyclo[3.2.1]octan-8-yl)carbamate (compound VI, 3.50 kg, 11.06 mol, 1.00 eq.) at 10° C.~20° C. The resulting suspension was degassed under vacuum and purged with $H_2$ three times, then heated to 50° C.~55° C. with stirring under $H_2$ (0.3 Mpa~0.4 Mpa) for 16 hours. The same batch size was duplicated three times and filtered through MCC pad to remove the catalyst after being combined. The filtrate was concentrated by azeotrope with n-heptane (10.00 L) twice and then mixed with n-heptane (10.00 L). The mixture was heated to 50° C.~55° C. with stirring for 16 hours and then cooled down to 20° C.~30° C. to form a suspension. The solid was collected by vacuum filtration and rinsed with n-heptane (5 L) twice. The resulting wet cake was dried under vacuum for 20 hours at 45° C.~50° C. to afford tert-butyl N-(3-azabicyclo[3.2.1]octan-8-yl)carbamate (compound (I), 6.00 kg, 26.51 mol, 80% yield, 99.38% purity) as a white solid.

Compound (I): $^1$H NMR: (400 MHz, DMSO) δ ppm: 6.49 (s, 1H), 3.284-3.293 (d, 1H), 2.48-2.57 (m, 5H), 1.89 (s, 2H), 1.66-1.68 (m, 2H), 1.40-1.42 (d, 2H), 1.34 (s, 9H).

The invention claimed is:

1. A process for preparing a compound of formula (I),

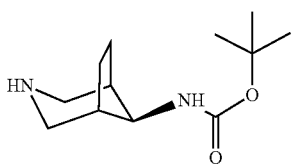

or a pharmaceutically acceptable salt thereof, the process consisting of:
  a) the imine formation of compound (III),

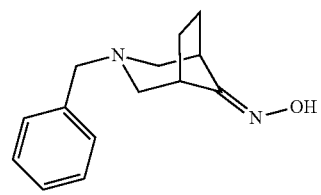

via reaction of compound (II),

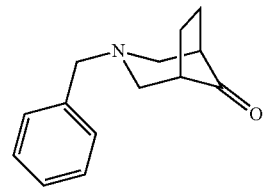

and hydroxylamine hydrochloride;
  b) formation of compound (IV),

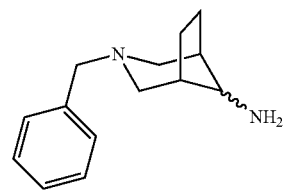

via reduction reaction from compound (III);
  c) salt formation of compound (V),

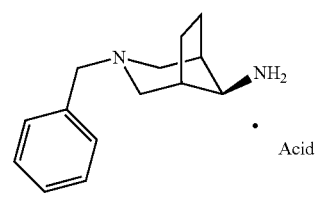

from compound (VI) and Acid, wherein Acid is selected from:

D-glutamic acid, (R)-(–)-mandelic acid, 1-hydroxy-2-naphthoic acid, citric acid, 4-aminosalicylic acid, L-tartaric acid, hippuric acid, malonic acid, glutaric acid, oxalic acid, fumaric acid, succinic acid, 4-aminobenzoic acid, 2,5-dihydroxybenzoic acid, L-malic acid, salicylic acid, maleic acid, (1S,3R)-(–)-camphoric acid, pamoic acid, mucic acid, palmitic acid, oleic acid and lactobionic acid;

d) formation of compound (VI),

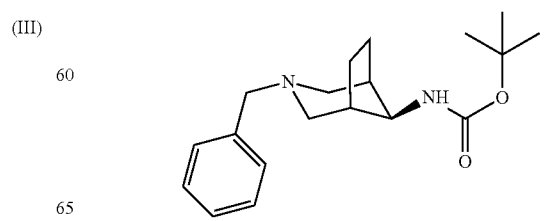

via dissociation and boc-protection of compound (V); and
e) formation of compound (I),

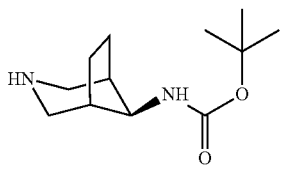
(I)

via de-protection of compound (VI).

2. The process of claim 1, characterized in that the formation of the compound (IV) in b) is performed in the presence of a reducing reagent at 0° C.-70° C., wherein the reducing reagent is selected from Na, Pd/c and Raney-Ni.

3. The process according to claim 1, characterized in that Acid used in c) is (R)-(−)-Mandelic acid, and the amount of (R)-(−)-Mandelic acid used in c) is 0.1-2.0 eq.

4. The process according to claim 1, characterized in that the compound (VI) synthesized in d) is purified through recrystallization, which was performed in a solvent, wherein the solvent is selected from n-heptane, hexane and petroleum ether.

5. The process according to claim 1, characterized in that the de-protection reaction in e) is performed at 20° C.-100° C.

6. A process for preparing a compound of formula (I),

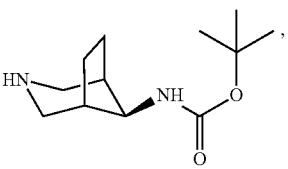
(I)

or a pharmaceutically acceptable salt thereof, the process comprising:
salt formation of compound (V),

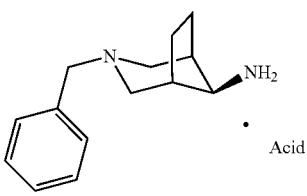
(V)

from compound (VI),

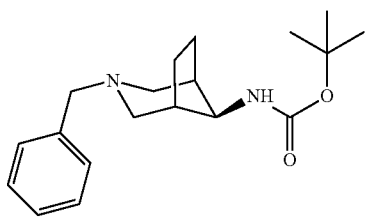
(VI)

and Acid,
wherein the Acid is selected from: D-glutamic acid, (R)-(−)-mandelic acid, 1-hydroxy-2-naphthoic acid, citric acid, 4-aminosalicylic acid, L-tartaric acid, hippuric acid, malonic acid, glutaric acid, oxalic acid, fumaric acid, succinic acid, 4-aminobenzoic acid, 2,5-dihydroxybenzoic acid, L-malic acid, salicylic acid, maleic acid, (1S,3R)-(−)-camphoric acid, pamoic acid, mucic acid, palmitic acid, oleic acid and lactobionic acid.

7. The compound of formula (V),

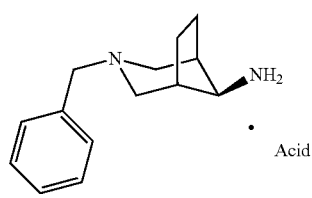
(V)

wherein Acid is selected from: D-glutamic acid, (R)-(−)-mandelic acid, 1-hydroxy-2-naphthoic acid, citric acid, 4-aminosalicylic acid, L-tartaric acid, hippuric acid, malonic acid, glutaric acid, oxalic acid, fumaric acid, succinic acid, 4-aminobenzoic acid, 2,5-dihydroxybenzoic acid, L-malic acid, salicylic acid, maleic acid, (1S,3R)-(−)-camphoric acid, pamoic acid, mucic acid, palmitic acid, oleic acid, and lactobionic acid.

8. A compound which is an adduct of exo-3-Benzyl-3-azabicyclo[3.2.1]octan-8-amine and (R)-(−)-mandelic acid, having formula Va

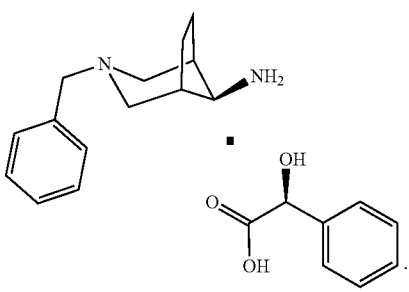
(Va)

9. The process of claim 1, wherein Acid is (R)-(−)-mandelic acid.

10. The process of claim 2, wherein the formation of the compound (IV) is performed in the presence of Raney-Ni at 20° C.-30° C.

11. The process of claim 3, wherein the amount of (R)-(−)-mandelic acid used in c) is 0.6 eq.

12. The process of claim 4, wherein the solvent is n-heptane.

13. The process of claim 5, wherein the de-protection reaction in e) is performed at 65° C.-75° C.

14. The process of claim 6, wherein the acid is (R)-(−)-mandelic acid.

* * * * *